US008135452B2

(12) United States Patent
Dougherty et al.

(10) Patent No.: US 8,135,452 B2
(45) Date of Patent: Mar. 13, 2012

(54) RAPID 3-DIMENSIONAL BILATERAL BREAST MR IMAGING

(75) Inventors: Lawrence Dougherty, Wenonah, NJ (US); Hee Kwon Song, Moorestown, NJ (US); Raymond Charles Boston, West Chester, PA (US); Mitchell Schnall, Wayne, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 701 days.

(21) Appl. No.: 12/288,463

(22) Filed: Oct. 20, 2008

(65) Prior Publication Data
US 2009/0105582 A1 Apr. 23, 2009

Related U.S. Application Data

(63) Continuation of application No. PCT/US2007/009824, filed on Apr. 23, 2007.

(60) Provisional application No. 60/793,799, filed on Apr. 21, 2006.

(51) Int. Cl.
*A61B 5/05* (2006.01)
(52) U.S. Cl. ......... 600/420; 600/407; 600/408; 600/410
(58) Field of Classification Search .................. 600/407, 600/408, 410, 420, 425
See application file for complete search history.

(56) References Cited

U.S. PATENT DOCUMENTS

| 5,363,845 | A | 11/1994 | Chowdhury |
| 6,363,275 | B1 | 3/2002 | Kaiser |
| 6,411,837 | B1 | 6/2002 | Fischer |
| 6,468,231 | B2 | 10/2002 | Sarvazyan |
| 6,919,722 | B2 | 7/2005 | Angelos |

FOREIGN PATENT DOCUMENTS
WO PCT/US2007/009824 4/2007

OTHER PUBLICATIONS

Altbach et al., "A Post-processing Method for Obtaining Accurate T2 Estimates from a Single Radial Fast-spin Echo K-space Data Set," Proc. ISMRM, 11th Annual Meeting, p. 1070 (2003).
Blaimer et al., "SMASH, SENSE, PILS, GRAPPA How to Choose the Optimal Method," Top. Magn. Reson. Imaging 15(4):223-236 (2004).
Dougherty et al., "Parametric Mapping of Contrast Kinetics from Rapid Radial MR-DCE Breast Images," Abstract, ISMRM 14th Scientific Meeting and Exhibition, Seattle, May 2006.
Dougherty et al., "Simultaneous Bilateral 3D DCE-MR Breast Imaging with Radial Acquisition," ISMRM 13th Scientific Meeting and Exhibition, p. 86, Miami Beach, May 2005.
Dougherty et al., "High Frame-Rate Simultaneous Bilateral DCE-MR Breast Imaging," Magn. Reson. Med., 57:220-225 (2007).
Friedman et al., "SENSE Imaging of the Breast," AJR 184:448-451 (2005).

(Continued)

*Primary Examiner* — Brian Casler
*Assistant Examiner* — Rajeev Siripurapu
(74) *Attorney, Agent, or Firm* — Woodcock Washburn, LLP

(57) ABSTRACT

Provided is a method for rapid, 3D, dynamic, projection reconstruction bilateral breast imaging using simultaneous multi-slab volume excitation and radial acquisition of a contrast enhanced bilateral image, in conjunction with SENSE processing, using k-Space Weighted Image Contrast ("KWIC") filtering and multi-coil arrays for signal separation in an interleaved bilateral MR bilateral breast scan that uses conventional Cartesian sampling without parallel imaging. Software was developed for the reconstruction, modeling contrast kinetics using a heuristic model, display by parametric mapping and viewer/analysis of the multidimensional, high frame-rate bilateral breast images.

17 Claims, 7 Drawing Sheets

OTHER PUBLICATIONS

Heywang et al., "MR Imaging of the Breast using Gadolinium-DTPA," J. Comput. Assist. Tomogr. 10:199-204 (1986).
Heywang et al., "MR Imagining of the Breast with Gd-DTPA: Use and Limitations," Radiology 171:95-103 (1989).
Jones et al., "K-Space Substitution: A Novel Dynamic Imaging Technique," Magn Reson Med. 29:830-834 (1993).
Joseph et al., "Experimental Simulation Evaluation of ECG-gated heart scans with a small number of views." Med. Phys. 10(4):444-449 (1983).
Kaiser et al., "MR Imaging of the Breast: Fast Imaging Sequence with and without Gd-DTPA," Radiology 170:681-686 (1989).
Korosec et al., "Time-Resolved Contrast-Enhanced 3D MR Angiography," Magn. Reson. Med. 36:345-351 (1996).
Kuhl et al., "Dynamic Breast MR IMaging: Are Signal Intensity Time Course Data Useful for Differential Diagnosis of Enhancing Lesions?," Radiology 211:101-110 (1999).
Larkman et al., "Use of Multicoil Arrays for Separation of Signal from Multiple Slices Simultaneously Excited," J. Magn. Reson. Imaging 13:313-317 (2001).
Lee et al., "MR Imaging Screening of the Contralateral Breast in Patients with Newly Diagnosed Breast Cancer: Preliminary Results," Radiology 226(3):773-778 (2003).
Lethmate et al., "Dynamic magnetic resonance imaging with radial scanning: a post-acquisition keyhole approach," Magma 16(1):21-28 (2003).
Li et al., "Kinetic Assessment of Breast Tumors Using High Spatial Resolution Signal Enhancement Ration (SER) Imaging," Magn. Reson. Med., 58:572-581 (2007).
Lucht et al., "Classification of signal-time curves from dynamic MR mammography by neural networks," J. Magn. Reson. Imaging 19(1):51-57 (2001).
Mistretta et al., "3D Time-Resolved Contrast-Enhanced MR DSA: Advantages and Tradeoffs," Magn. Reson. Med. 40:571-581 (1998).
Moate et al., "A modified logistic model to describe gadolinium kinetics in breast tumors" J. Magn. Reson. Imaging 22:467-473 (2004).
Mussurakis et al., "Dynamic Contrast-Enhanced Magnetic Resonance Imaging of the Breast Combined with Pharmacokinetic Analysis of Gadolinium-DTPA Uptake in the Diagnosis of Local Recurrence of Early Stage Breast Carcinoma," Investigative Radiology 30(11):650-6214 (1995).
Nunes et al., "Breast MR Imaging: Interpretation Model," Radiology 202:833-841 (1997).
Nunes et al., "Update of Breast MR Imaging Architectural Interpretation Model," Radiology 219(2):484-494 (2001).
Orel et al., "Suspicious Breast Lesions: MR Imaging with Radiologic-Pathologic Correlation," Radiology 190:485-493 (1994).
Parrish et al., "Continuous Update with Random Encoding (CURE): A New Strategy for Dynamic Imaging," Magn. Reson. Med. 33:326-336 (1995).
Peters et al., "Undersampled Projection Reconstruction Applied to MR Angiography," Magn. Reson. Med. 43:91-101(2000).
Proksa et al., "Multi-resolution MRI." In: Proc 5th Scientific Meeting ISMRM, Vancouver, Canada 1997, p. 1933.
Pruessmann et al., "SENSE: Sensitivity Encoding for Fast MRI," Magn. Reson. Med. 42(5):952-962 (1999).
Rasche et al., "Continuous Radial Data Acquisition for Dynamic MRI," Magn. Reson. Med. 34:754-761 (1995).
Riederer et al., "MR Fluoroscopy: Technical Feasibility," Magn. Reson. Med. 8:1-15 (1988).
Schnall et al., "A Combined Architectural and Kinetic Interpretation Model for Breast MR Images," Academic Radiology 8(7):591-597 (2001).
Sodickson et al., "Simultaneous Acquisition of Spatial Harmonics (SMASH): Fast Imaging with Radiofrequency Coil Arrays," Magn. Reson. Med. 38(4):591-603 (1997).
Song et al., "k-Space Weighted Image Contrast (KWIC) for Contrast Manipulation in Projection Reconstruction MRI," J. Magn. Reson. Med. 44(6):825-832 (2000).
Song et al., "Dynamic MRI With Projection Reconstruction and KWIC Processing for Simultaneous High Spatial and Temporal Resolution," J. Magn. Reson. Med. 52(4):815-824 (2004).
Song et al., "Simultaneous Acquisition of Multiple Resolution Images for Dynamic Contrast Enhanced Imaging of the Breast," Magn. Reson. Med. 46(3):503-509(2001).
Song et al., "A Technique for High Spatial and High Temporal Resolution Dynamic MRI: Temporal KWIC," Proc. Intl. Soc. Mag. Reson. Med. 11:2110 (2004).
Szabo et al., "Application of artificial neural networks to the analysis of dynamic MR imaging features of the breast," European Radiology 14(7):1217-1225 (2004).
Van Den Brink et al., "Implications of SENSE MR in routine clinical practice," European J. Radiology. 46(1):3-27 (2003).
Van Vaals et al., ""Keyhole" Method for Accelerating Imaging of Contrast Agent Uptake," J. Magn. Reson. Imag. 3:671-675 (1993).
Vigen et al., "Undersampled Projection-Reconstruction Imaging for Time-Resolved Contrast-Enhanced Imaging," J. Magn. Reson. Med. 43:170-176(2000).
Vomweg et al., "Improved artificial neural networks in prediction of malignancy of lesions in contrast-enhanced MR-mammography," Medical Physics 30(9):2350-2359 (2003).
International Preliminary Report on Patentability, PCT/US07/09824. Oct. 22, 2008.
International Search Report, PCT/US07/09824. May 19, 2008.
Written Opinion, PCT/US07/09824. May 19, 2008.

--Prior Art--

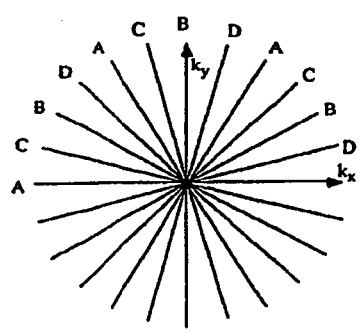
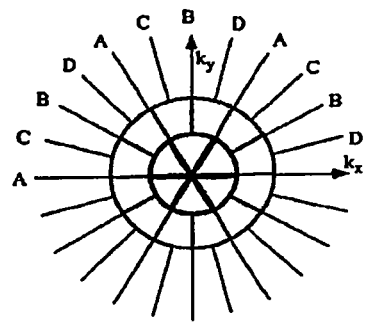
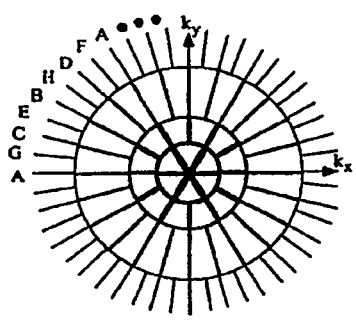
FIG. 3A    FIG. 3B    FIG. 3C
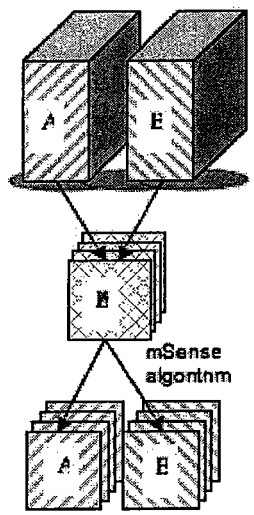
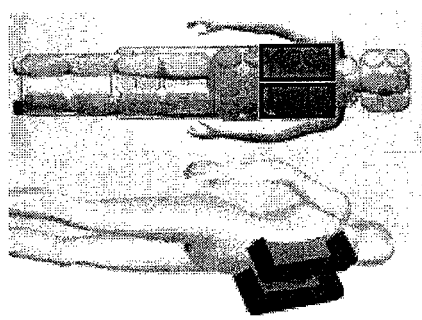
FIG. 4A    FIG. 4B

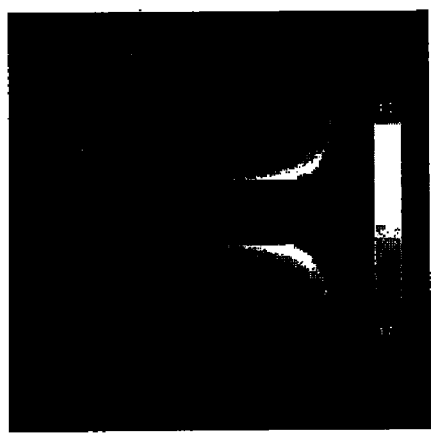
FIG. 5
 
FIG. 6A        FIG. 6B

FIG. 7A        FIG. 7B        FIG. 7C
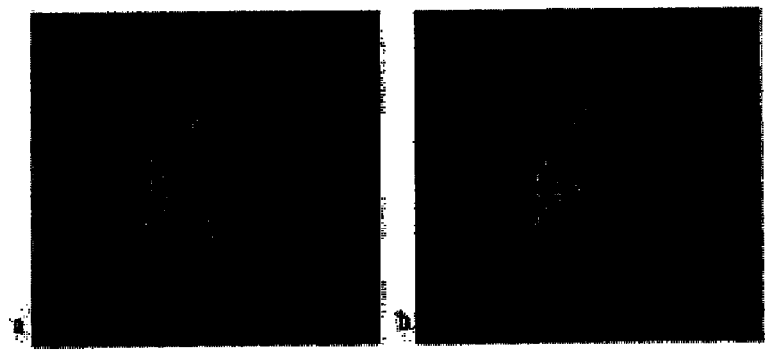
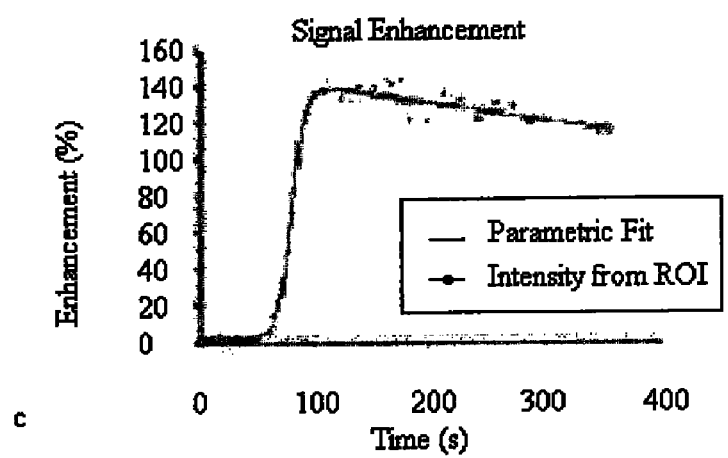
FIG. 8

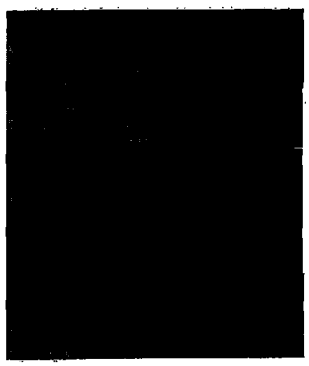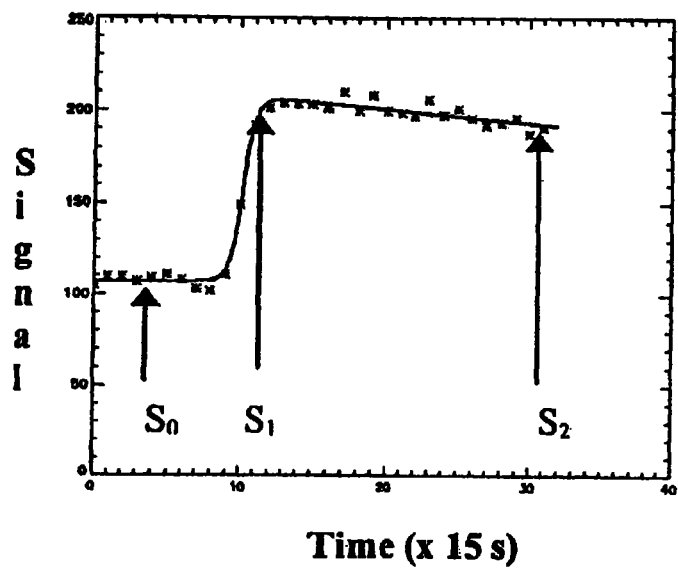
FIG. 10A
FIG. 10B

RAPID 3-DIMENSIONAL BILATERAL BREAST MR IMAGING

CROSS REFERENCE TO RELATED APPLICATIONS

This application is a continuation of International Application PCT/US2007/009824 filed Apr. 23, 2007, published as WO 2007/124151, which claims priority to U.S. Provisional Application No. 60/793,799 filed Apr. 21, 2006, each of which is incorporated herein in its entirety.

GOVERNMENT INTEREST

This invention was supported in part by Grant No. R01-CA-90699 from the National Institutes of Health. Accordingly, the Government may have certain rights in this invention.

FIELD OF THE INVENTION

The present invention relates to a rapid, bilateral projection reconstruction method for 3D dynamic contrast-enhanced Magnetic Resonance Imaging ("MRI" or "MR imaging") of both breasts of an individual simultaneously, providing high-resolution images, as well as rapid sampling of the contrast kinetics.

BACKGROUND OF THE INVENTION

Breast cancer is the most frequently diagnosed malignancy among women other than skin cancer, and the second leading cause of mortality in women (following lung cancer). The American Cancer Society estimates that over 200,000 new invasive cases of breast cancer will occur each year, and more than 40,000 deaths from breast cancer among women in the United States. Early detection is the most important factor to survival, with a survival rate of 96%, if the cancer is found early. As a result, breast MR imaging has become of more interest in the past years, and it is now a tool that is widely used in clinical routine as an important method to assess especially the difficult cases, where conventional mammography and ultrasound are at their limits.

Mammography has been found to often miss breast cancer in its early stages when it is most amenable to treatment and most likely to be cured. Between 10-30% of women who have breast cancer and undergo mammography have negative mammograms, and in about two-thirds of these cases, the radiologist failed to detect retrospectively evident cancer. Such misses have been attributed to the subtle nature of the visual findings, poor image quality, or oversight by the radiologist. Mammography is also disadvantageous in that it is limited in individuals who have breast implants, and is not as accurate in younger individuals whose breast tissue tends to be denser. In addition, mammography exposes individuals to ionizing radiation that may increase their risk of developing breast cancer. Mammography also requires significant compression of the breast tissue that many individuals find painful, leading them to avoid mammography.

Magnetic Resonance Imaging (MRI) has become an important non-invasive medical technique over the past decade. For example, U.S. Pat. No. 6,411,837 discloses a method for high-resolution magnetic resonance tomography of the female breast, U.S. Pat. No. 6,468,231 discloses a method and device for detecting changes in mechanical and structural properties of breast tissue, and U.S. Pat. No. 6,363,275 discloses a device for detecting and for treating tumors using differential diagnosis. Each is herein incorporated by reference.

MR imaging uses a strong direct current magnetic field in conjunction with tunable gradient magnetic fields to spatially control locations at which the net sum magnetic field reaches a pre-selected value. As the magnetic bias fields are varied spatially, a series of radio frequency (RF) pulses are applied. When the RF energy is at a resonance frequency of sample atoms of a particular species and surroundings, those sample atomic nuclei absorb the RF energy and are excited to a higher spin state. The excited spin state then decays to a lower energy state of excitation and the decay is accompanied by an emission of an RF pulse. The RF of a nucleus (nuclear magnetic resonance, or "NMR"), and its resulting signal depend on a number of factors, including mass, density, dipole moment, relaxation frequency, as well as chemical bonding and electrostatic potential of its surroundings. To enhance the contrast between tissues within an organism, one or more contrast agents may be introduced into an individual's body prior to MRI analysis.

The NMR signals are detected using one or more radiofrequency (RF) "coils." The term "coil" is also commonly used to refer to the electrical part of the device and its housing or support structure. The size of the local coil is kept small to allow them to be easily fit to the patient on the MRI device, and to enable imaging of only the imaging volume of interest, since imaging regions that are not required adds noise to the acquired signal unnecessarily. However, the smaller the size of the local coil, the smaller its field of view, or sensitivity profile. Imaging of larger areas using the smaller coils requires the use of multiple small coils, either simultaneously in a combined manner or by moving the coil between imaging acquisitions. Such coils can be operated individually or as multi-coil arrays. Combining signals from multiple coils can yield improvements in SNR. However, one of the challenges associated with using multiple coils for imaging is the fact that the fields of individual coils may interact, resulting in coil-to-coil coupling. Such interactions tend to reduce the coil quality factor, or Q.

Dynamic contrast enhanced MR (DCE-MRI) breast imaging has shown promising results in its ability to detect breast abnormalities (Heywang et al., *J. Comput. Assist. Tomogr.* 10:199-204 (1986); Kaiser et al., *Radiology* 170:681-686 (1989); Heywang et al., *Radiology* 171:95-103 (1989); Orel et al., *Radiology* 190:485-493 (1994)). Architectural features visible after enhancement have a high correlation with cancer (Nunes et al., *Radiology* 202:833-841 (1997); Nunes et al., *Radiology* 219(2):484-494 (2001)) and the enhancement dynamics have also been shown to be highly correlative with benign or malignant lesions (Kuhl et al., *Radiology* 211:101-110 (1999)). However, there previously had to be a decision to either acquire MRI data with high temporal and low spatial resolution, or data with high spatial and low temporal resolution. Combined interpretations have been shown to improve diagnostic performance over each separate approach (Schnall et al., *Academic Radiology* 8(7):591-597 (2001); Vomweg et al., *Medical Physics* 30(9):2350-2359 (2003); Szabo et al., *European Radiology* 14(7):1217-1225 (2004)). However, even for a unilateral breast study, the simultaneous acquisition of both high spatial resolution data for architectural analysis and high temporal resolution data for contrast kinetic classification is difficult due to their diverging demands (Dougherty et al., ISMRM 13th Scientific Meeting and Exhibition, page 86, Miami Beach, May 2005).

The high-resolution imaging needed to distinguish features necessary for architectural interpretation requires a relatively long time to acquire. For example, to image the entire breast, a 3-dimensional acquisition of 32 slices with a sampling matrix of 512×384, takes ~2 minutes in a typical clinical exam. Acquiring fewer slices or reducing the matrix size will speed acquisition but at the cost of coverage or spatial resolution. The importance of using a high frame rate for enhancement dynamics analyses was shown by (Lucht et al., *J. Magn. Reson. Imaging* 19(1):51-57 (2001)), who have reported a significant increase in diagnostic performance when using 28 points as compared to three time points.

Keyhole rectilinear k-space acquisitions have also been proposed (van Vaals et al. *J. Magn. Reson. Imag.* 3:671-675 (1993); Jones et al., *Magn Reson Med* 29:830-834 (1993)). In the keyhole technique, only the low spatial frequencies along the phase encoding direction are acquired at short intervals, and the full resolution images are reconstructed by using the high spatial frequencies from a reference dataset. However, this acquisition scheme causes the mixing of the constantly updated low spatial frequency data with the high frequency data acquired at different time periods, potentially resulting in blurring of the enhancing structures in the phase encoding direction. Other related acquisition schemes have been developed to help reduce these artifacts (Parrish et al., *Magn. Reson. Med.* 1995; 33:326-336 (1995); Korosec et al., *Magn. Reson. Med* 36:345-351 (1996); Mistretta et al., *Magn. Reson. Med.* 40:571-581 (1998)). However, the inevitable mixing of old and new data that are non-contiguous in time still occur, and may cause measurement errors.

A further consideration with coil systems is their ability to operate in a parallel MR imaging mode. Parallel imaging methods, such as SMASH (Sodickson et al., *Magn. Reson. Med.* 38(4):591-603 (1997)) or SENSE (Pruessmann et al., *Magn. Reson. Med.* 42(5):952-962 (1999)) have gained attention in the last few years as methods to reduce scan time, and thus, improve temporal resolution without sacrificing spatial resolution. In these approaches, spatial information carried by the placement of multiple receiver coils can be used to reduce the number of phase encoding steps required for traditional spatial encoding. Based on the sensitivity profiles of these coils operating independently, a reconstruction algorithm can be implemented that enables reconstruction of a full image volume in a fraction of the conventional image acquisition time.

Researchers have shown reduction factors of 2-3 using SENSE encoding in application to breast imaging (van den Brink et al., *European J. Radiology.* 46(1):3-27 (2003); Friedman et al., *AJR* 184:448-451 (2005)). Larkman et al. (*J. Magn. Reson. Imaging* 13:313-317 (2001A)) have previously described the use of multi-coil arrays for separation of signals from multiple, simultaneously excited slices, but was not adapted to multiple 3D volumes. With such parallel imaging methods, temporal resolution can be increased. However, with greater acceleration factors the SNR is concomitantly decreased and the time resolution is still insufficient to adequately sample the contrast kinetics. Dougherty et al., "Parametric Mapping of Contrast Kinetics from Rapid Radial MR-DCE Breast Images," Abstract, ISMRM 14th Scientific Meeting and Exhibition, Seattle, May 2006.

Under-sampled radial imaging has also been investigated as a way to reduce imaging time (Joseph et al., *Med. Phys.* 10(4):444-449 (1983); Peters et al., *Magn. Reson. Med.* 43:91-101(2000); Vigen et al., *J. Magn. Reson. Med.* 43:170-176(2000)). It has been shown that the number of projections can be greatly reduced using this method, while preserving spatial resolution and reducing the scan time. Further, by interleaving the radial acquisitions, a method that allows image reconstruction at two different resolutions has also been described (Proksa et al., "Multi-resolution MRI." In: *Proc 5th Scientific Meeting ISMRM*, Vancouver, Canada 1997, p 1933). Expanding on this approach, a method that allows one to arbitrarily choose from among several combinations of temporal/spatial resolutions during postprocessing was developed for unilateral breast imaging (Song et al., *Magn. Reson. Med.* 46(3):503-509(2001)). This flexibility is accomplished by strategically interleaving multiple undersampled projection reconstruction datasets, in which each set can be used to reconstruct a high temporal resolution image. Images with increasingly higher spatial resolutions can subsequently be formed by combining two or more interleaved datasets.

In 3-dimensional DCE imaging of breast lesions using the Song technique, it was demonstrated that various combinations of image matrix size (sampling points×number of views) and temporal resolution can be reconstructed. Using this technique, 64×64 images (using 48 projections) can be acquired every 12 seconds, 128×128 (96 projections) every 24 seconds, 256×256 (192 projections) every 48 seconds, or 512×512 (384 projections) every 96 seconds. However, the main drawback of this technique is also its strength—that is, the temporal/spatial resolution tradeoff. Due to SNR limitations and the desire for artifact-free images, high spatial resolution images required lower temporal resolution since a greater number of views were needed during reconstruction.

To simultaneously achieve both high spatial and high temporal resolutions in a single dynamic image series, Song et al., (*J. Magn. Reson. Med.* 52(4):815-824 (2004)) used a weighted radial view sharing scheme (KWIC) that preserved spatial resolution, temporal resolution and image quality.

As the value of DCE-MR of the breast is appreciated by clinicians, its usage is likely to increase, and there will be a demand for bilateral breast acquisitions. However, the problem of imaging at a high frame rate while preserving spatial resolution is compounded in the case of bilateral imaging. In a clinical bilateral exam the acquisitions are often interleaved, which doubles the scan repetition rate (TR) and reduces the temporal resolution. A coarse representation of the contrast kinetics is the best that can be achieved with this type of acquisition. In another approach often used clinically, the breasts are scanned with individual unilateral studies on consecutive days with a significant penalty in cost and patient inconvenience.

As a result, while these methods offered a significant improvement, alone they cannot achieve the temporal resolution needed to adequately sample the enhancement curve, while simultaneously acquiring high spatial resolution images of both breasts. Thus, until the present invention, there has been a need for an effective and more accurate method for the bilateral screening of both breasts, particularly for use in high-risk screening, cancer staging, and for potentially reducing the number of breast biopsies. Availability of an easy to employ, more accurate methodology for such testing will lead to vast improvement in early and accurate diagnosing with the lowering of the morbidity and mortality of breast cancer.

SUMMARY OF THE INVENTION

In light of the foregoing stated needs in the art, the present invention provides a bilateral projection reconstruction method for 3D dynamic contrast-enhanced MR imaging of both breasts simultaneously of an individual. "Projection reconstruction" (PR) is a method of image reconstruction that uses views of an object acquired at different angles ("radial acquisition"). Using a unique sequence approach, this new method comprises at least three elements: radial sampling, k-space weighted image contrast (KWIC), and simultaneous excitation. Thus, the present invention adds parametric mapping (color overlay) and a viewer/analysis program to evaluate the multidimensional data using the pulse sequence/reconstruction/heuristic model, thereby providing the small set of images from which radiologists were able to rapidly identify cancers in a manner not previously possible.

Using a double-side band modulation of the RF excitation pulse, discontinuous volumes ("slabs") that include both breasts were simultaneously selected. The number of slice phase encoding steps was under-sampled by a factor of 2 and the resulting signal aliasing from one volume to the other was removed using SENSE processing. In-plane encoding used an interleaved radial acquisition reconstructed using dynamic KWIC temporal filtering. Image resolution was 0.5×0.5×3.0 mm with an effective temporal resolution of 15 seconds for both breast volumes. Combined with the 2× acceleration from SENSE encoding, this provided a 16× acceleration factor over a conventional MR bilateral breast scan.

An initial evaluation of these methods was performed on a cohort of women presenting with palpable or mammographically visible breast abnormalities. Seventy-three abnormalities were found in 45 of the 54 bilateral examinations that were performed, and in 11 of those cases, there was a significant finding in the contralateral breast. Thus, it was confirmed that dynamic contrast enhanced images of both breasts can be acquired, simultaneously providing high-resolution images, as well as rapid sampling of the contrast kinetics.

The present high resolution bilateral MR imaging techniques offer significant advantages in the field of breast cancer screening, including, e.g.: (1) the improved ability to detect early breast cancers; (2) the improved ability to differentiate between breast cancer and normal breast tissue; (3) the improved ability to differentiate between breast cancer and benign lesions in the breast; (4) the improved ability to differentiate between scar and recurrent breast cancer; (5) the improved detection of multifocal and/or multicentric breast cancers; (6) the improved ability to determine the extent of breast cancer present; (7) the improved ability to detect early breast cancer in individuals with breast implants; (8) the improved ability to detect breast cancer in individuals with breast implants while also evaluating the breast implants for abnormalities; and (9) the improved ability to detect early breast cancer in individuals with dense breasts.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE DRAWINGS

The foregoing summary, as well as the following detailed description of the invention, will be better understood when read in conjunction with the appended drawings. It should be understood, however, that the invention is not limited to the precise arrangements and instrumentalities shown.

FIG. 2A shows rectilinear acquisition. FIG. 2B shows radial acquisition of the present invention.

FIGS. 3A-3C are schematic drawings showing interleaved sets of projections. FIG. 3A shows a four-subaperture acquisition strategy for dynamic KWIC temporal filtering, wherein interleaved sets of projections (A through D) were acquired sequentially. In acquisition A which makes up the first subaperture, views are spread evenly between 0° and 180° (for full echo acquisition). For the next subaperture B, the view angles are rotated such that they bisect those of A. Subsequent subapertures C and D bisect A and B. This alternating acquisition scheme is repeated (ABCDABCD . . . ) throughout the entire dynamic process. FIG. 3B shows reconstruction, wherein only a single subaperture (A) is utilized in the central k-space core, while two time-contiguous acquisitions fill the adjacent annular region (A and B). The outer-most k-space region is contributed by all four subapertures that make up one full data set. FIG. 3C shows a data acquisition and weighting scheme for an 8-subaperture series.

FIGS. 4A and 4B depict how data is acquired. FIG. 4A shows how data acquired from slabs A and B simultaneously, can produce a combined dataset. By applying the iPAT mSENSE algorithm, slices from each slab can be reconstructed, if at least two coil elements are positioned along the slabs. FIG. 4B shows clinical positioning of slabs covering at least two coil elements along the slab direction.

FIG. 5 is a geometry factor map of breast coil array showing a coronal slice through the center of the volume. The g-factors are highest in the medial slices particularly in the posterior region where g-max=1.5.

FIGS. 6A-6B show post-contrast breast MR images acquired using simultaneous acquisition embodiments of the present invention. FIGS. 6A and 6B are paired imaging slices showing a benign lesion in the right breast (FIG. 6B). Images were dynamic-KWIC processed to have a 15 second effective temporal resolution.

FIGS. 7A-7C show posterior regions of the medial slices aliasing into the contralateral breast. FIG. 7A is an uncorrected MR breast image showing aliasing of signal from the contralateral breast. FIG. 7B shows the same slice corrected using SENSE processing. FIG. 7C separately shows the aliased component of the image. The intensity of image 7C is scaled independently for display.

FIGS. 8A-8C show a post-contrast phase of a case with an enhancing lesion that was shown to be malignant upon biopsy. FIG. 8A shows a post-contrast breast image with a malignant lesion. FIG. 8B is a color overlay of the P1 parameter from a pixel-by-pixel, 5-parameter fit. FIG. 8C shows time vs. signal intensity data from a region of interest (ROI) placed in the most enhancing region of the lesion with a parametric fit.

FIG. 10A-10B show a representative post-contrast breast image (FIG. 10A) with a malignant lesion and the time signal intensity with the fitted curve on the same plot. $S_0$, $S_1$, and $S_2$ are time points at which signal intensities are used to calculate the signal enhancement ratio (SER). FIG. 10B is a time/signal intensity plot with fitted curve superimposed. Contrast injection was initiated after the 8th time point.

DESCRIPTION OF PREFERRED EMBODIMENTS OF THE INVENTION

Figure 1:
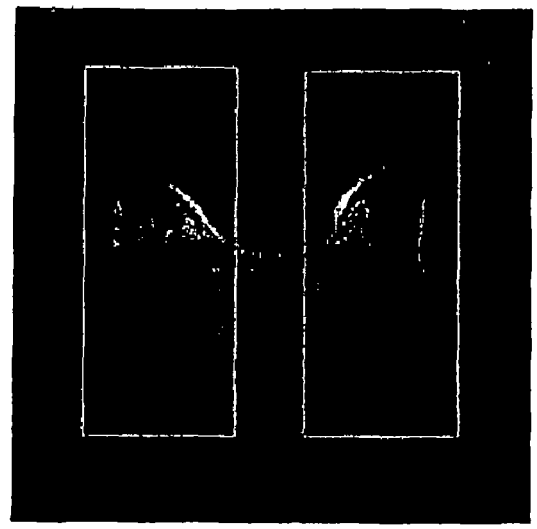
FIG. 1 is an image of an MR localizer showing bilateral breast prescription.

The present invention provides methods for rapid, 3D, bilateral breast imaging using a simultaneous multi-slab volume excitation in conjunction with SENSE processing, using k-Space Weighted Image Contrast ("KWIC") and multi-coil arrays for signal separation. These methods were combined with the dynamic KWIC approach to achieve an acceleration factor of 16× (2× from SENSE and 8× from KWIC) over an interleaved bilateral MR bilateral breast scan that uses conventional Cartesian sampling without parallel imaging. Additionally, software was developed for the reconstruction, display and analysis of the high frame-rate bilateral breast images. The term "rapid" is given its ordinary meaning, i.e., the present imaging methods acquires data faster than methods in the prior art. "3D" also is used in a manner standard to three dimensional imaging.

An initial evaluation of these methods was performed on a cohort of women presenting with palpable or mammographically visible breast abnormalities. Thus, the present invention also provides methods of detecting breast cancer for use in high-risk screening and cancer staging where the screening includes performing MRI in accordance with the methods disclosed herein on such individuals; and determining from this present MRI methods whether those individuals have indications of breast cancer.

As used herein, the term "breast cancer" refers to a condition characterized by anomalous rapid proliferation of abnormal cells in one or both breasts of a subject. "Bilateral" refers to both breasts, whereas "contralateral" refers to the opposing breast. "Primary" refers to the breast with the suspicious mass. The abnormal cells often are referred to as "neoplastic cells," which are transformed cells that can form a solid tumor. The term "tumor" refers to an abnormal mass or population of cells (i.e., two or more cells) that result from excessive or abnormal cell division, whether malignant or benign, and pre-cancerous and cancerous cells. Malignant tumors are distinguished from benign growths or tumors in that, in addition to uncontrolled cellular proliferation, they can invade surrounding tissues and can metastasize. In breast cancer, neoplastic cells may be identified in one or both breasts only, and not in another tissue or organ, and/or in one or both breasts and one or more adjacent or nonadjacent tissues or organs (e.g., lymph nodes) into which the breast cancer cells have metastasized.

Normal risk individuals are those who do not have a significant family history of breast cancer and have not otherwise been told by a physician that for whatever reason they have a high risk of acquiring breast cancer due to genetics, behavior or other characteristic. Asymptomatic individuals have neither detected a suspicious lump by breast self examination, mammography and/or ultrasound, nor have they experienced any of the other symptoms of breast cancer, such as nipple discharge, breast pain or architectural distortion of the breast. Conversely, "symptomatic individuals" have experienced or identified at least one of the foregoing symptoms of breast cancer. By comparison, "high risk" when combined with screening and cancer staging, refers to individuals that have had a prior diagnosis or history of breast cancer, have two or more close relatives that have had breast or ovarian cancer, show a mutation in the BRCA1 or BRCA2 gene, or received radiation therapy between 12 and 18 years of age. The disclosed methods are applicable to a imaging a cancer belonging to any group of cancers without limitation, e.g., leukemias, lymphomas, meningiomas, mixed tumors, adenomas, carcinomas, adenocarcinomas, sarcomas, and the like. Individuals referred to herein are human patients of either sex, but normally female, but the method is further intended to encompass the bilateral imaging of any mammal.

The methods of the invention are novel in the way they examine the function of the breast tissue as well as its structure. For a cancer to grow it must establish its own blood supply in a process called angiogenesis. In angiogenesis, the cancer will form new blood vessels that are unlike any normally found in the breasts of adults. In particular, these angiogenic blood vessels demonstrate abnormal physiologic function which is distinguishable from that of normal adult blood vessels found in non-cancerous tissue.

Institutional Review Board (IRB) approval was obtained prior to the start of this study, and women with suspicious breast abnormalities were included to confirm the effectiveness of the methods of the present invention. After informed consent, patients were placed in the scanner (1.5 T (Tesla) Siemens Sonata, Siemens Medical Systems, Iselin, N.J.) in the prone position, with the breasts gently compressed within a receive-only breast coil (Siemens Medical Systems) which uses a single element for each breast. While the present invention is not intended to be limited to this, or any specific scanner or coil, the example is provided to illustrate one effective application of the invention in real-life testing, but in the alternative, it could be implemented with any whole-body or dedicated MR scanner. Additionally, other coil sets with different multi-coil configurations could also be utilized in accordance with the manufacturer's methods or with methods well known in the art.

Contrast Agents

In certain embodiments of the methods of the invention, cancer in an individual's breast can be identified with the aid of contrast agents that are administered so that enhancement behavior of the breast tissue is evaluated by the MRI methods. Performing simultaneous bilateral breast examinations preserves the high temporal resolution and eliminates the need for a second administration of a contrast agent (as would be needed in a subsequent examination of the contralateral breast. In the presently disclosed embodiment, a high-resolution baseline volume was acquired from both breasts, followed by dynamic imaging, which was started simultaneously in each breast with an intravenous injection of 0.1 mmol/kg gadopentetate dimeglumine (Magnevist, Berlex Laboratories, Wayne, N.J.).

Contrast agents were administered by injection, over a 10 second interval, followed by a saline flush, but any recognized method of administration is intended. The method described is not limited by the use of a particular dose, injection rate or particular contrast agent selected, since many are known in the art and continue to be developed, but for the purposes of enablement, dosages typically range from 0.05 mmol/kg to 0.3 mmol/kg body weight of the individual, administered at recognized, physiologically-acceptable rates and manner. The term "physiologically acceptable" refers to the administration of a contrast agent which is compatible with any other ingredients of the pharmaceutical composition, which is not deleterious to the subject to which the composition is administered in an "amount sufficient" to provide the contrast necessary to utilize the MR imaging methods described herein.

Contrast agents, which may be used in accordance with the present invention, include suitable contrast agents known to those in the art. Such contrast agents may be as simple as water, but substances with specific magnetic properties are preferred. Most commonly, a paramagnetic metal ion, such as manganese, iron, or gadolinium, including chelates of gadolinium, are used. Gadolinium compounds do not routinely cross the blood-brain barrier unless the barrier has broken down due to, e.g., tumors or infections, and anaphylactic reactions are rare, occurring in only about 0.03-0.1% of the cases in which it is used. Nevertheless, in certain embodiments, dialysis soon after the scan is completed may be used to promptly remove the agent from the body. Gadolinium-enhanced tissues and fluids appear extremely bright on T1-weighted images. This provides high sensitivity for detection of angiogenic vascular tissues (e.g., tumors).

As exemplified, in selected embodiments of the invention, a secondary injection (or other form of administration) may be administered into the individual of a physiological saline solution or other suitable fluid of about the same volume as that of the contrast agent may also be used, so that the contrast agent reaches the blood circulation as completely as possible. Such a saline flush, is routinely used in the administration of MRI contrast agents, is typically given following the contrast agent and in an amount approximately equal to the dose of the contrast agent, or in amounts and concentrations recognized in the art.

By performing a dynamically enhanced MRI with T1 weighting of the breast over a period of approximately 10 minutes, or over ranges of time extending from 2 to 10 minutes, 3 to 8 minutes, or 5-6 minutes at specific intervals, such as intervals of approximately every 5 to 90 seconds, or approximately every 60 seconds, cancer from normal breast tissue can be differentiated with a very high degree of sensitivity and specificity. The dynamically enhanced MRI may be started within 0-120 seconds, or approximately 40 seconds from the time the injection of the contrast agent is started. Following administration of the contrast agent, subsequent MRI imaging through the breast is then acquired at approximately 5 second to 90 second intervals, or approximately 60 second intervals. By this method, the degree of percentage of MRI signal enhancement over time may be evaluated, and the percentage of enhancement versus time curve may be plotted.

Regions of cancer growth within the breast demonstrate a significantly higher degree of enhancement than surrounding normal breast tissue early after contrast agent administration and this degree of enhancement tends to decreases more quickly than that of the normal tissue. Typically there is a rapid response to the contrast agent and then a slower later response. This difference in enhancement is a direct effect of the differing physiology of the cancer's angiogenic blood vessels.

In certain embodiments of the invention, post-contrast data were acquired over the 6 minute period following administration of the contrast agent, or for a period sufficient to observe the contrast wash-out rate. Total exam time was ~20 minutes, which time may vary depending on the specific imaging protocol, and as per manufacturer's suggestions or recognized practices in the MRI arts. The examination included T1-weighted (TR/TE, 500/5) spin-echo, fat-saturated T2-weighted (4000/105) fast spin-echo, and coil reference acquisitions that preceded the baseline and dynamic contrast series.

Imaging

In Gradient Echo Imaging (also known as field echo imaging, echo planar imaging, low angle imaging, or flip imaging) contrast relationships are controlled not only by TR and TE, but by an additional factor called the flip angle, which usually begins as less than 90° (the flip angle is important in determining contrast relationships). Thus, the signal is refocused, not by using 180° pulses as in spin echo imaging, but by altering the magnetic fields in the bore of the imager. This is achieved by reversing whichever side of the magnet is of higher magnetic field strength, and whichever is lower (gradient reversal). One needs to understand TR, TE, and flip angle relationships when performing imaging in the pulse sequence family known as field echo or gradient echo imaging.

For Inversion Recovery (IR) imaging the radio frequency pulse sequence is 180°-90°-180°. In inversion recovery, the time between successive 180°-90°-180° trains is the TR value. The time between the middle 90° RF pulse and the second 180 degree pulse is called the TE time or echo time. With inversion recovery, the time of inversion (TI) is the time between the first 180° pulse and the middle 90° pulse. Contrast is, in part, controlled by altering the TI value. For example, by using a very short TI value, the fat, or adipose tissue, signal intensity can be suppressed, which can be quite useful when looking at tissue for infection or tumor. IR imaging is used to suppress fat in the "spectral inversion" described below.

Spoiled gradient echo sequences use a spoiler gradient on the slice select axis during the end module to destroy any remaining transverse magnetization after the readout gradient, which is the case for short repetition times. These types of sequences also use semi-random changes in the phase of radio frequency pulses to produce a spatially independent phase shift. As a result, only z-magnetization remains during a subsequent excitation. Spoiled gradient recalled acquisition in the steady state technique has proven to be superior to conventional post-contrast spin echo (SE) techniques for MRI detection of tumors. Recent studies have shown that the standard T1-weighted spin echo (SE) technique for magnetic resonance imaging (MRI) fails to identify 40% of certain tumors, but using soft tissue contrast agents with thinner sections and spoiled gradient recalled acquisition in the steady state (SPGR) significantly improved the sensitivity and confidence level.

In the presently disclosed embodiment, the contrast-enhanced images were acquired using a fast, 3D, spoiled gradient-recalled projection reconstruction sequence using 512 data samples/projection with 384 projections, and 32 phase encoding steps in the slice direction. Other imaging parameters were: repetition time (TR)=9.8 ms; echo time (TE)=4 ms; flip angle=20°; and the sampling bandwidth was 260 Hz/pixel, although other imaging parameters recognized in the art are also effective in the present invention and are included herein. (Hz=Hertz, unit of frequency. Pixel, short for picture element, is a single point in a graphic image. The intensity of each pixel is variable; in color systems. For example, each pixel has typically three or four dimensions of variability, such as red, green and blue, or cyan, magenta, yellow and black).

In certain embodiments, imaging volumes encompassing the breasts ("breast volumes") were chosen using the graphic prescription tool that is part of the scanner's user interface (FIG. 1) in this embodiment. The frequency of the RF slab-select pulse was set to excite the center point between both breasts and modulated by a cosine function ("double sideband modulation") at a frequency that positioned a slab over each breast. The signal from fat was suppressed using a spectral inversion pulse played-out on every 16th repetition. The images were acquired using a 24 cm FOV (field of view) and ~3 mm thick slices in the sagittal plane (an x-z plane, perpendicular to the ground).

Breasts are typically scanned in the sagittal plane, which is the most efficient in terms of spatial encoding. With gentle compression in the left/right direction the slab thickness is usually less than 10 cm, and most of the slices fill the FOV.

The slab thickness, slice thickness and FOV are selected to encompass each breast entirely, depending on breast size. Scanning in the transverse plane would allow both breast to be imaged simultaneously, but this would require a larger FOV. The transverse plane divides the body into cranial and caudal (head and tail) portions (for post-embryo humans a coronal plane is vertical and a transverse plane is horizontal, but for embryos and quadripeds a coronal plane is horizontal and a transverse plane is vertical), such that when describing anatomical motion, these planes describe the axis along which an action is performed, meaning that for the transverse plane, movement travels from head to toe. Given sufficient receiver bandwidth and data handling capability, the FOV could be encoded just as rapidly as a smaller FOV, but due to the geometry of the breast, the slab thickness would typically double, increasing the scan time.

Simultaneously Excitement of Parallel Regions and Signal Acquisition

When scanning the breasts sagittally, the number of acquisition steps (the number of phase-encoding steps in the z-direction) can be cut in half by simultaneously exciting two parallel regions. If a conventional reconstruction were used, the signal from one breast would be superimposed on the other ("aliasing") since the number of slice phase-encoding steps was half of that required to unambiguously reconstruct all 64 slices (32 from each breast).

Aliasing is an artifact that occurs in MR images when the scanned body part is larger than field of view (FOV), i.e., the incorrect mapping of tissue signals from outside the FOV to a location inside the FOV. This is caused by the fact, that the acquired k-space frequency data is not sampled density enough. The cyclical property of the Fourier transform fills the missing data of the right side with data from behind the FOV of the left side and vice versa, therefore the spectrums will overlap, resulting in a replication of the object in the x-direction. Over-sampling in frequency direction, done by increasing the sampling frequency, prevents this aliasing artifact. The proper frequency, based on the sampling theorem, must be at least twice the frequency of each frequency component in the incoming signal. All frequency components above this limit will be aliased to frequencies between zero and half of the sampling frequency, which combined with the proper signal information, creates the artifact. Aliasing in the frequency direction can be eliminated by sampling of the signal at a rate twice as fast, or by applying frequency specific filters to the received signal.

A similar problem can occur in the phase encoding direction (the slice direction in this case), where the phases of signal-bearing tissues outside of the FOV are a replication of the phases that are encoded within the FOV. Phase encoding gradients are scaled for the field of view only, and as a result, unless corrected, tissues outside the FOV do not get properly phase encoded, relative to their actual position and "wrap" into the opposite side of the image.

Over-sampling creates a larger field of view, and as a result more data needs to be stored and processed, which for modern MRI systems is not really a problem. However, over-sampling in phase direction (no phase wrap) increases the number of phase encoding steps, results in longer scan/processing times.

Aliasing in the slice encoding direction can be overcome by using the same algorithms, as used in the parallel acquisition ("iPAT") techniques, if there are at least two coil elements in the slab direction. See FIG. 4A. Depending upon the distance of a coil element to each slab, the signal being received by this coil element varies. If this distance dependency, i.e., the "coil sensitivity," is known, the contribution of each slab to the measured signal intensity can be retrieved, and two separate images can be reconstructed. SENSE processing, which takes advantage of the coils' sensitivities to different regions of the image volume, is offered by many companies in slightly modified implementations: e.g., Philips (SENSE), Siemens (mSENSE), General Electric (ASSET), and Toshiba (SPEEDER).

Using this simultaneous excitation technique, the standard breast coil can be used to achieve an acceleration factor of 2, providing the additional advantage of increasing the spatial resolution without impacting the temporal resolution. Another advantage, compared to 'standard' iPAT techniques, which can also be accelerated in the slab direction, is that it does not require the slab(s) to cover a contiguous region. So, two distant areas can be acquired simultaneously. See FIG. 4B.

In the present embodiment, coil sensitivity maps were generated from reference scans in which the data were acquired using a conventional low-resolution acquisition. The reference images were acquired by scanning each breast volume sequentially using the breast multi-coil. The signals received from each channel of the breast coil were reconstructed separately and the sensitivity map for that coil was computed by taking the complex ratio of these images.

Although the multi-coil that was used in this study used a single channel for each breast, many designs use multiple coils that are situated to the medial and lateral side of each breast. This embodiment of the present approach to bilateral imaging has the advantage of having a higher effective frame rate for the characterization of contrast dynamics, and it can also be used to reduce total scan time. The Examples below demonstrates the diagnostic capabilities of the embodied breast imaging methods.

As can be seen in the localizer image (FIG. 1), the in-plane FOV was positioned posteriorly in order to acquire all of the breast tissue that curved around the lateral side of the patient and also to visualize potentially enhancing lymph nodes that may be located posterior to the breast. In this slab position, the spins from the medial chest region would normally need to be encoded in the acquisition. Using the methods of the present invention, however, the region of the chest between the breasts was eliminated from the acquisition by selecting discontinuous volumes. This reduced the volume by ~⅓ and allowed for a subsequent reduction in the number of slice phase encoding steps. The increased spatial resolution allows the visualization of high anatomic detail, and therefore delivers an increased diagnostic specificity. However, even with the elimination of the medial volume from the acquisition and good coil geometry-factors, some signal aliased into the contralateral volume, until the acquisition method was modified.

Radial Acquisition and Under-Sampling

Figure 2A:
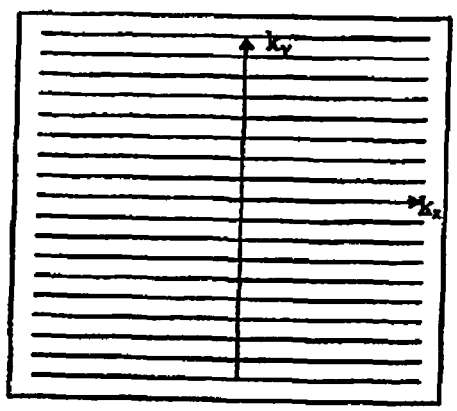
FIGS. 2A and 2B are schematic drawings showing imaging acquisition patterns.
Figure 2B:
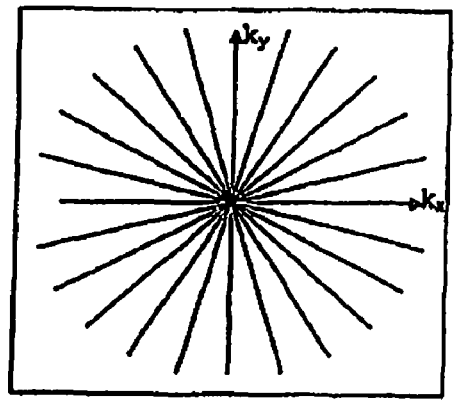
Figure 9:
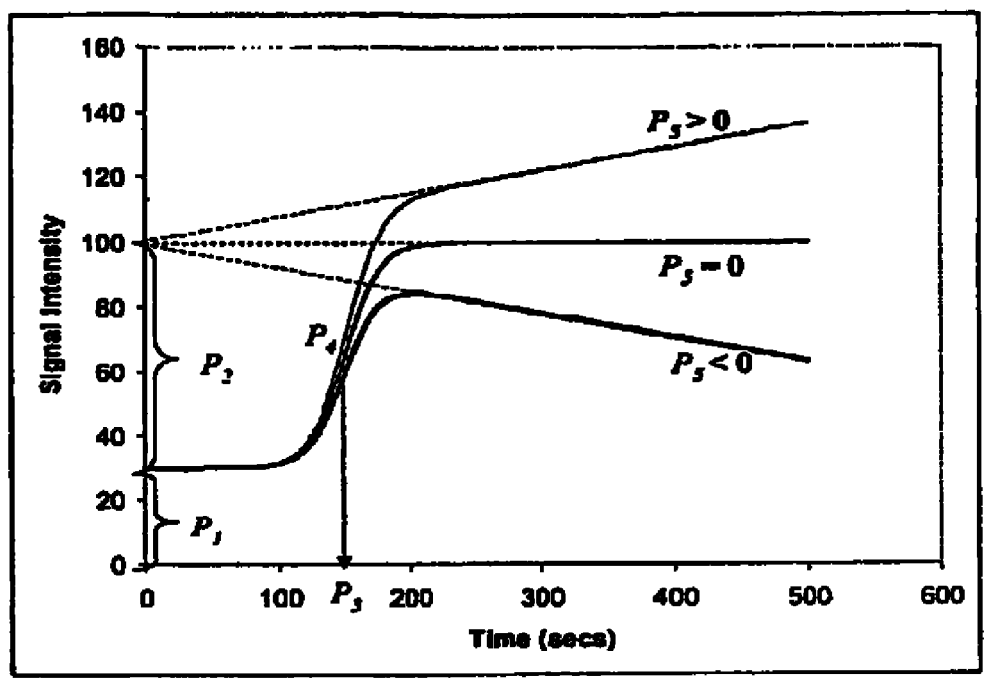
FIG. 9 is a schematic drawing showing the derivation of the parameters of the modified logistic model from the dynamic signal intensity curve SI(t) obtained during a magnetic resonance examination of a breast tumor. $P_1$ represents the baseline signal, $P_5$ is the terminal slope ($sec^{-1}$); $P_2$ is equivalent to the a signal intensity obtained at the intersection of the zero time signal axis and a tangent drawn from the terminal portion of the signal intensity curve, minus $P_1$; $P_3$ (sec) is the time of the maximum slope and $P_4$ ($sec^{-1}$) is the maximum slope.
Figure 11:
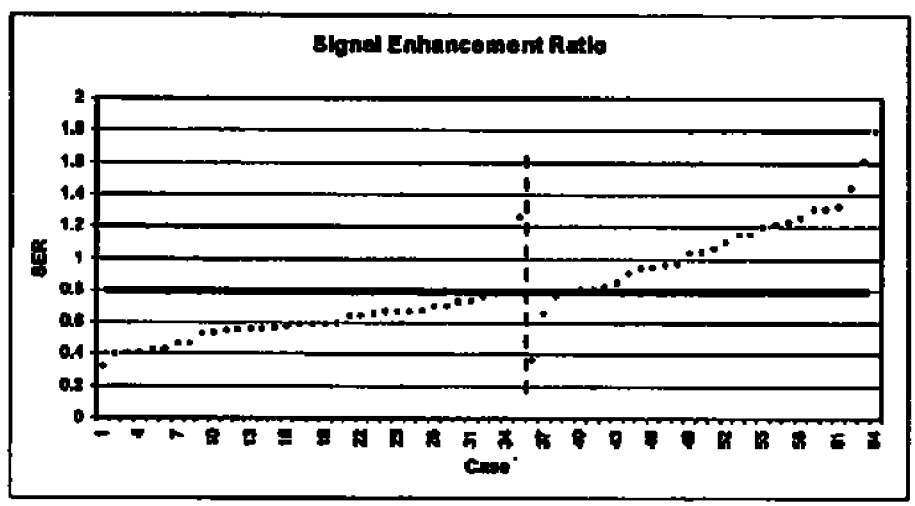
FIG. 11 is a plot of 64 enhancing lesions from each reader, from which time signal intensity plots were measured and fitted. Signal enhancement ratio (SER) was calculated and plotted for each case, and a ratio 0.8 was chosen as the cutoff between benign (<0.8) (left of dashed line) and malignant (≧0.8) lesions (right of dashed line).

An express element of the present invention is "radial acquisition" of the samples in k-space (FIG. 2B), rather than acquisition in the rectilinear fashion of the prior art (FIG. 2A). Each interleaf (or subaperture) consists of a highly under-sampled PR data set for rapid imaging in which the views are equally spaced between 0° and 180° for a full echo acquisition, or between 0° and 360° for a half-echo readout (compare, for example, with Joseph et al., *Med. Phys.* 10(4):444-449 (1983); Peters et al., *Magn. Reson. Med.* 43:91-101 (2000); Vigen et al., *Magn. Reson. Med.* 43:170-176 (2000)). In contrast to rectilinear sampling, where the spatial resolution depends on the number of phase encoding lines, in radial sampling spokes are spread evenly to form a 'wheel,' and only the resolution along the readout direction of the 'spokes' determines the resolution. In other words, resolution in radially-sampled imaging is determined not by the number of views, but by the readout resolution (Joseph et al., supra 1983). Increasing the resolution has only a minimal impact on the overall scan time. Therefore, the temporal resolution of a radial scan only depends upon the number of 'spokes,' and can be reduced to a fraction of the time required for a full rectilinear dataset. However, the number of 'spokes' influences the image quality.

Streaking artifacts often occur in images with a highly reduced number of 'spokes' and the signal to noise drops as the square root of number of 'spokes.' If the 'spokes' are acquired interleaved in time, full spatial resolution datasets can be reconstructed using either all lines at lower temporal resolution, or using only reasonable subsets of the lines yielding multiple high temporal resolution images (see FIGS. 3A-3C). Acquisition with four interleaves begins with acquisition A, and then for the next interleaf B, the 'wheel' is rotated to cover the area between the spokes of A. For example, in a four-interleaf acquisition sequence, following the acquisition of the first subaperture A (see FIG. 3A), the next subaperture B is acquired, such that its views bisect those of A. Subsequent subapertures C and D bisect A and B (see FIG. 3A). These four subapertures make up one full data set (see FIG. 3B). Thus, for dynamic imaging, multiple full data sets are acquired in tandem $(A_1 B_1 C_1 D_1 A_2 B_2 C_2 D_2 \ldots)$ to sufficiently sample the dynamic process. The subaperture factor, $\alpha$, represents the number of interleaves that comprise a full data set. The number of interleaves can be extended as shown in FIG. 3C, in which eight are prescribed.

During acquisition, data were collected in eight 48 view under-sampled passes, covering $\pi$ radians in each pass. The view angles were interleaved, so that subsequent passes bisected the views of earlier ones (Song et al., *J. Magn. Reson. Med* 44(6):825-832 (2000)). The number of view within each interleaf may be varied depending of the angle interleaving scheme (e.g., reverse binary, golden angle, or random ordering).

In an alternative embodiment, any non-Cartesian k-space trajectory that over-samples the central region could be used in place of radial sampling. The invention is also not limited to gradient recalled echoes. Spin echoes, free-induction-decay readout, and multi-echoes approaches could also be used.

MRI data are collected in the spatial frequency domain (k-space). In most imaging scenarios, scan time is directly related to the number of data samples needed for proper reconstruction. In other words, as time progresses the signal traces out a trajectory in k-space with the velocity vector of the trajectory that is proportional to the vector of the applied magnetic field gradient. By the term "effective spin density" is meant the true "spin density" ($\rho(\vec{x})$) corrected for the effects of T1 preparation, T2 decay, dephasing due to field inhomogeneity, flow, diffusion, etc. and any other phenomena that affect that amount of transverse magnetization available to induce signal in the RF probe. From the basic k-space formula, it follows immediately that an image ($I(\vec{x})$) is reconstructed simply by taking the inverse Fourier transform of the sampled data viz.

$$(I(\vec{x})) = \int d^3 \vec{k} \, S(\vec{k}(t)) \cdot e^{-2\pi i \vec{k}(t) \vec{x}}$$ Equation 1

Using the k-space formalism, a number of seemingly complex ideas become simple. In a standard spin echo or gradient echo scan, where the readout (or view) gradient is constant (e.g., $G_x$), a single line of k-space is scanned per RF excitation. When the phase encoding gradient is zero, the line scanned is the $k_x$ axis. When a non-zero phase-encoding pulse is added in between the RF excitation and the commencement of the readout gradient, this line moves up or down is k-space, i.e., the line $k_y$=constant is scanned. The k-space formalism also makes it very easy to compare different scanning techniques. Since alternate lines of k-space are scanned in opposite directions, this must be taken into account in the reconstruction. In each shot, a different interleaved segment is acquired, and the shots are repeated until k-space is sufficiently well-covered. Since the data at the center of k-space represent lower spatial frequencies than the data at the edges of k-space, the TE value for the center of k-space determines the image's T2 contrast.

The importance of the center of k-space in determining image contrast can be exploited in the present imaging techniques. Typically, the k-space sampling density is set by the Nyquist criterion based on the image resolution and field of view (FOV). Since $\vec{x}$ and $\vec{k}$ are conjugate variables (with respect to the Fourier transform), the Nyquist theorem may be used to show that the step in k-space determines the FOV of the image (maximum frequency that is correctly sampled) and the maximum value of k sampled determines the resolution, i.e., $$FOV \alpha \frac{1}{\Delta k} \text{Resolution } \alpha |k_{max}|$$ Equation 2

These relationships apply to each axis (x, y and z) independently.

The MRI data acquisition can be accelerated by under-sampling k-space, i.e., simply collecting fewer data samples. However, typically when k-space is under-sampled, the Nyquist criterion is violated, and Fourier re-constructions exhibit aliasing artifacts. Over-sampling is the increase in data to avoid aliasing and wrap-around artifacts. Since PR data are oversampled in the central k-space region in accordance with the present invention, such filtering is allowable as long as the sampling density remains within the Nyquist limits. The radius $\rho_1$ of this central region can be computed from the Nyquist criterion, and can be shown to be equal to $$\rho_1 = \frac{N}{\pi \cdot a}$$ Equation 3 where N is the number of views for one full data set. For example, for N=256 total views and $\alpha$=8, a circular region with a radius of 10 k-space points would define the k-space core region filled with only the desired subaperture.

In the adjacent annular k-space region, data from two time-contiguous subapertures are used (that which fills the central core, plus one which bisects it), while the outer-most region contains data from all subapertures that make up a complete high-resolution data set. It can be shown that the outer radius of the first annular region is $2*\rho_1$. This graded weighting scheme allows a smooth temporal transition between the center-most and outer k-space regions, and can help alleviate artifacts that may arise from k-space signal modulations due to the dynamic processes. The data in each k-space subdivision must be appropriately weighted to maintain proper density throughout k-space. In the acquisition shown, for example, in FIG. 3B, the central core data must be multiplied by a factor of 4, and the annular region by 2.

The KWIC Method for Dynamic MR Imaging

In the embodied invention, a second key component is that data from each breast coil were saved separately and reconstructed using a re-gridding approach with dynamic k-Space Weighted Image Contrast ("KWIC") view sharing. The KWIC method for dynamic MR imaging, developed by the inventors (Song et al., supra, 2000; Song et al., *Proc. Intl. Soc. Mag. Reson. Med.* 11:2110 (2004); Song et al., supra, 2004, the contents each of which are herein incorporated by reference) enables the acquisition of a series of images with both high temporal and high spatial resolution. KWIC view sharing combines data from multiple interleaves to reconstruct one image; but instead of combining all data, only pieces of the interleaves are used. The technique, which is based on the projection reconstruction (PR) imaging scheme, utilizes distinct data acquisition and reconstruction strategies.

While Lethmate et al. (*Magma* 16(1):21-28 (2003)), reported a dynamic imaging keyhole technique, referred to as the "core only" scheme, only the inner-most k-space core region is filled with a single subaperture, while the full data set is used throughout the rest of k-space. In contrast, the present invention demonstrates that the dynamic KWIC technique is temporally more accurate than the "core only" scheme. This is because the dynamic KWIC technique utilizes the "angle bi-section" (or reverse binary) strategy to determine the order in which the data are acquired. This acquisition scheme in turn determines the manner in which the views are weighted throughout k-space. In essence, the angle bi-section strategy allows the use of fewer views throughout k-space, particularly in the central k-space regions (and therefore have improved temporal selectivity), while simultaneously fulfilling the Nyquist criterion.

During KWIC acquisition, data are collected in multiple under-sampled passes, with the view angles interleaved in such a way that those of subsequent passes bisect the views of earlier ones. With judicious data filtering, the image contrast of an image reconstructed using multiple adjacent passes could be made to be dominated by a single pass. The KWIC technique makes use of the fact that the central region of k-space in radially-acquired data is over-sampled, allowing a choice of different data weights to enhance or reduce the amount that each view contributes to the k-space core (FIG. 3B), which dominates image contrast. The technique was initially implemented into a fast spin-echo (FSE) sequence, and was used to reconstruct multiple T2-weighted images from a single image data set. When the KWIC strategy is used for a dynamic image series, the effective temporal resolution is equivalent to that of a highly under-sampled radial technique, but the image quality is equivalent to that of a fully acquired high spatial resolution image. The effectiveness of dynamic KWIC has been demonstrated in both simulations and in vivo, high-resolution, contrast-enhanced imaging of breast lesions.

The KWIC technique is also beneficial in terms of the signal-to-noise, because it uses data from a number of projections typically required for a high-quality, high spatial resolution image, rather than from only a single pass.

One consequence of the KWIC filtering scheme is the potential "pairing up" of image contrast in a dynamic image series, particularly of small objects. The effect is substantially reduced when $\rho_1$ is increased to 32, such that a larger k-space core is dominated by a single subaperture. Although streaking artifacts may become more noticeable at low intensity, high image quality is still maintained and the effect on ROI measurements is small. It may also be possible to alleviate this effect by including data from other subapertures in the annular regions, such that the 'average time' in each k-space subdivision is equivalent, somewhat similar to the 'average TE' scheme suggested for improved T2 relaxation mapping in the original KWIC technique (Altbach et al., *Proc. ISMRM*, 11th Annual Meeting, p. 1070 (2003)). It should be noted that in spite of this potential "pairing" effect, the proposed weighting scheme remains temporally more precise than the previous techniques which use either all subapertures of the full data set ("core only") or temporally discontinuous data (conventional keyhole method) immediately outside the central k-space region.

A dynamic time series is formed using a sliding window reconstruction (Riederer et al., *Magn. Reson. Med* 8:1-15 (1988); Rasche et al., *Magn. Reson. Med* 34:754-761 (1995)), such that the subsequent images in the dynamic series are reconstructed using the previous data set with the earliest subaperture replaced with the next in the series. The data are weighted such that the subaperture that encodes the k-space core is at or near the center of the subaperture group. For example, for $\alpha=8$ data set, the first image would comprise the first 8 subapertures $A_1B_1C_1D_1E_1F_1G_1H_1$, where D is in bold-faced type to indicate that it encodes the k-space core. The second image in the series would be comprised of $B_1C_1D_1E_1F_1G_1H_1A_2$, followed by $C_1D_1E_1F_1G_1H_1A_2B_2$, and so on. The total number of images in the series will then be $(F-1)*\alpha+1$, where F is the number of full data sets acquired in the dynamic series. Thus, if four full data sets are acquired in succession with $\alpha=8$, there will be 25 images in the temporal series, with the first image corresponding to the time point at which the fourth subaperture (D1) is acquired.

In an embodiment of the invention for bilaterial imaging, five baseline frames (pre-contrast) and 20 mid- and post-contrast frames were reconstructed using the dynamic KWIC method in combination with the parallel acquisition of both breast image volumes, yielding an effective temporal resolution of 15 seconds for each frame. This results in a 16×-acceleration factor over a non-accelerated interleaved bilateral acquisition. However, these the resulting images qualities are nearly identical to those acquired with the Cartesian-sampled FSE sequence at different effective echo times, and T2 maps can be generated from a single image data set of a fully sampled high-spatial resolution data set. Unlike conventional under-sampled PR methods that also allow higher temporal resolution, the dynamic KWIC technique is less susceptible to low image SNR or image degradation due to streaking artifacts. Moreover, in comparison to conventional rectilinear keyhole techniques, dynamic data are continually updated throughout the entire k-space, creating image data that are time-contiguous, and reducing the likelihood of data misregistration.

A major advantage of the KWIC acquisition strategy is that many of the decisions regarding optimum reconstruction, such as the size of the central core or the various annular regions in which increasing number of passes are added, can be made retrospectively, since the same data set can be used for the various methods of image reconstruction.

Parallel MRI Reconstruction

A geometry factor map (FIG. 5), showing the regional noise amplification due to SENSE processing, was computed from the reference images, as described by Pruessmann et al., supra, 1999, herein incorporated by reference. An important improvement in the MR imaging art for increasing imaging speed has been the development of parallel MRI (pMRI). Scan time has been reduced and it is applicable to almost any available MRI method. The pMRI reconstruction methods can roughly be classified into two groups. Those in which the reconstruction takes place in image space (e.g., SENSE, PILS) comprise an unfolding or inverse procedure, and those in which the reconstruction procedure is done in k-space (e.g., SMASH, GRAPPA), comprise a calculation of missing k-space data. SENSE processing and other reconstruction methods are reviewed by Blaimer et al., *Top. Magn. Reson. Imaging* 15(4):223-236 (2004).

The SENSE algorithm has to be repeated for every pixel location in the reduced FOV image to finally reconstruct the full FOV image. SENSE provides pMRI with arbitrary coil configurations, however, at the expense of some additional SNR loss, which depends on the underlying geometry of the coil array. The encoding efficiency at any position in the FOV with a given coil configuration can be analytically described by the so-called geometry factor (g-factor), which is a measure of how easily the matrix inversion can be performed. Thus, the SNR in the final SENSE image is additionally reduced by the g-factor.

With the placement of a separate receiver coil on each breast, the geometry factor was ~1.0 in most regions of the breast, which was close to the optimal situation, wherein each coil received signal from only those spins that could be resolved without aliasing. The geometry factors with the described coil arrangement were very good in most regions of the breast, with only a few regions in the medial slices and the area posterior to the chest wall exceeding 1.0. In the SENSE reconstruction, a threshold was used to determine if a pixel should be processed. Pixels with aliased signals <5% of the true signal intensities were not processed. This residual error was not visible within the images and the beneficial effect was that it excluded noise pixels from the unfolding process (Larkman et al., supra 2001B). A separate coil sensitivity map was generated for each breast examination. All signaling between the MRI and the coils currently takes place through the cables by way of an MRI connector, but given wireless technology, the signals would be transmitted via a similar wireless means.

When compared to other dynamic imaging methods, measurements were similar except during the dynamic stage of the enhancement curve. Because the under-sampled image series comprises the narrowest temporal window (one subaperture per image), its dynamic curve seems most accurate. However, one problem with the under-sampled method, is that in vivo images are often noisy, causing errors in measurement, particularly at baseline before signal enhancement occurs. The "full data" image set, which weighs the 8 subapertures in each image equally is, in fact, the least accurate, due to the intrinsic averaging of the subapertures. Thus, the dynamic signal is effectively convolved with an 8-subaperture-wide kernel, smoothing out any rapid changes.

By limiting the data in the central k-space region to a single subaperture, the "core only" reconstructed images more accurately follow the dynamic changes in the larger 20-pixel phantom than the "full data" series. However, this improvement vanished when tracking small objects, e.g., small tumors, because in the "core only" method, high-spatial frequency regions have a greater contribution to image contrast in smaller objects. Thus, the measured signal behaves similar to the "full data" image series. As a result, both dynamic-KWIC reconstructions were more accurate than the other techniques compared in this study. The advantage of dynamic KWIC over the "core only" method is more apparent in the smaller phantom, and not surprisingly, dynamic KWIC with a larger $\rho 1$ performs noticeably better. Nevertheless, although the under-sampled reconstruction performs best in these simulations, its images would also possess the lowest SNR and the worst level of streaking artifacts due to the high degree of under-sampling. In the under-sampled reconstruction, signal abnormalities in the background due to streaking artifacts can be seen. Although innocuous in this example of a single small phantom (because the streaks appear outside the phantom), such streaks would contaminate all other regions within the image FOV.

Because of the inhomogeneous view weighting of dynamically changing views in both dynamic KWIC and the "core only" methods, signal modulations appear in their profiles, particularly at the object's edges where high-spatial frequency data have greater contribution. Both the profiles and the measured signal averages generally improve with the dynamic KWIC multi-regional weighting scheme, and the improvement is augmented as larger portions of k-space become dominated by the desired time frames (larger $\rho_1$).

It is clear nonetheless from these results that the proposed dynamic KWIC technique is capable of producing images with a high temporal resolution, on the order of highly under-sampled PR images that require a fraction of the time for a full data (as little as one-eighth of the time in at least one example), while preserving the image quality near that of a fully sampled image set.

In comparison to an interleaved bilateral acquisition, there was no loss in SNR due to the reduced scan time from under-sampling the number of slice-encoding steps by a factor of two (Larkman et al., supra, 2001). Therefore, the SNR was the same as that from an interleaved acquisition in most of the breast images. However, as seen in FIG. 5, the coil geometry-factor was higher in the medial slices, as well as in the posterior region, which lowered the SNR 13%-41% in those regions.

The Heuristic Model to Describe Gadolinium Kinetics in Breast Tumors

A five parameter modified logistic equation (Moate et al., *J. Magn. Reson. Imaging* 22:467-473 (2004) was developed that describes the signal enhancement in magnetic resonance dynamic contrast enhanced imaging (MRI-DCE).

$$SI(t) = \frac{P_2 + (P_5 \cdot t)}{\{1 + \exp(-P_4 \cdot (t - P_3))\}} + P_1 \qquad \text{Equation 4}$$

In this heuristic model, $P_1$ is the baseline signal, $P_2$ is related to the magnitude of the peak signal enhancement, $P_3$ is the approximate time of the maximum rate of increase of signal, $P_4$ is related to the maximum rate of signal enhancement, and $P_5$ is the terminal slope of the signal enhancement curve.

In contrast to the compartmental model approach, heuristic models make no assumptions or inferences about the underlying physiology of a tumor, but simply attempt to describe the important features or attributes of the uptake of contrast reagents ("CR"), such as gadolinium-diethylene-triamine penta-acetic acid (Gd-DTPA), and the dynamic imaging of a variety of tumors. Such heuristic parameters include: (1) baseline signal enhancement, (2) rate of enhancement, (3) time to peak enhancement, (4) peak enhancement, and (5) terminal slope. Heuristic models focus on parameters 2-5 since these have been implicated in aiding the diagnosis of malignant tumors (Mussurakis et al., *Investigative Radiology* 30(11):650-6214 (1995)).

Regardless of the type of analysis of signal intensity curves, the ultimate aim is generally to use the information imbedded in these curves to improve the differential diagnosis of malignant and benign tumors. Manual data analysis may introduce unintended user bias. Gamma functions may not have the flexibility to describe all observed signal enhancement patterns.

The heuristic model presented here has the flexibility to accurately describe all of the MRI signal enhancement patterns thus far encountered. The structure of the model renders the parameters easily identified using nonlinear regression. Of the five primary parameters of the model, three (P2, P4 and P5) describe the principal attributes of the signal enhancement curve that have been shown to have diagnostic/prognostic value. Thus, the parameters have a very close association with the kinetics underlying the MRI signal intensity and the breast lesion status. However, the model makes no assumptions about the topology or kinetic mechanisms underlying the signal profile. Advantageously, the model can be routinely fitted to 100 or more subjects in about 30 seconds. Yet, the model can be run without the need for special kinetic or allied modeling software, i.e., it operates with any ordinary statistical package. As a result, the parameters of the heuristic model have been proven effective when used to accurately estimate a number of secondary parameters that have also been shown to have diagnostic value, and many associated indices of lesion structure are very easily derived from the model using simple algebraic manipulations (e.g., residence times, maximum enhancement, washout rate, signal-enhancement-ratio (SER), etc). For example, for calculation of SER, three points are selected from the fitted curve: $S_0$ is the baseline pre-contrast intensity, $S_1$ is the intensity at 60 seconds post-contrast, and $S_2$ is the intensity at 350 seconds. SER is calculated by: $SER=(S_1-S_0)/(S_2-S_0)$.

A custom computer program was written to allow the user to view the breast images and analyze the contrast kinetics. From the KWIC processed images the signal intensity data were obtained, transferred off-line and reconstructed to fit the heuristic model, herein incorporated by reference). The time signal enhancement curve could be shown for any user selectable ROI or the curve parameters could be generated for each pixel and shown as a color overlay on the breast images (FIG. 10).

For the first dynamic KWIC and "core only" reconstruction methods, a Nyquist determined $\rho_1=15$ was used. For the second dynamic KWIC reconstruction, the k-space subregions were once again more 'evenly' divided, radially ($\rho_1=32$). A region-of-interest for each lesion was manually outlined, the intensity curves plotted, and the data was subsequently fitted to the dynamic enhancement model for comparison. Color overlays of the parameter were applied for a pixel-by-pixel, 5-parameter fit. Red indicates a high probability of cancer, green a high probability of being benign, and blue indicates an indeterminate classification The images were reviewed by a clinical radiologist experienced in reading MR breast images, and a clinical report was generated. A finding was defined as a focal mass, a regional enhancement, a ductal enhancement, or an architectural distortion. The finding was further categorized as being: highly suspicious for malignancy; suspicious for malignancy; likely benign with recommended imaging follow-up; definitely benign; or normal (no lesion). Categorization was based on combined T1/T2 appearance, architecture, and enhancement kinetics. Enhancement kinetic curves (per pixel, region-of-interest or whole lesion) were available for interactive viewing, as were color-coded parametric maps. The radiologist may further determine the progress of the disease in the individual by comparing the images produced by the present rapid, bilateral method with previously recorded images of the same breast volume of the individual, where those breast images may be of any type useful for clinical purposes (e.g., digital, MRI, mammogram, sonogram, PET, etc).

The MRI device is coupled generally to viewing workstation, particularly to an archive processor for receiving and storing an archival dataset for long-term storage purposes or for other future reference. The archive may be a computer hard disk, or any tangible storage medium capable of storing two-dimensional image data. Storage media include, e.g., paper, film, magnetic disk, optical disk, digital/digitized records, magnetic tape, and non-volatile integrated circuit memory. The processor can be coupled to a printer, for example, to print the dataset onto paper or film. The various recording elements can segregate, aggregate, index, and allocate the archival datasets without departing from the scope of the preferred embodiments. For example, the different components (text comments, 2-D images, and annotations) can all be digitally stored in different places, and even on different machines or networks, and then associated with hyperlinks.

The present invention is further described by example, which is provided for purposes of illustration only, without intended limitation unless otherwise specified. The various scenarios are relevant for many practical situations, and are intended to be merely exemplary to those skilled in the art.

EXAMPLES

Example 1

Using the methods described herein, fifty-four (54) bilateral exams were performed on women with breast abnormalities, all with excellent image quality. For each case, 64 high-resolution slices (0.47×0.47 mm/pixel) and 25 temporal phases (5 baseline and 20 post-contrast) were reconstructed. The scan repetition time was set at 9.8 ms in this study in order to be compatible with a previous breast imaging study. The minimum TR for the sequence, at the same bandwidth, was actually 8.1 milliseconds, which provided an effective temporal resolution of 12.4 seconds. Given sufficient SNR, from, e.g., a high field scanner, the receiver bandwidth could be increased and the TR reduced even further to improve the temporal resolution. All reconstruction, image analysis and viewing were performed on a dual Xeon processor PC at 3.1 GHz.

Total time for each volunteer to be in the scanner was ~25 minutes, including patient set-up. FIGS. 6A-6B show a representative case including post-contrast images from each breast. Fat (adipose tissue) suppression worked well across both breast volumes in all cases, except one in which the prescan tuning was performed incorrectly. However, baseline subtraction of the pre-contrast series still enabled analysis of that case.

As shown in FIG. 7, posterior regions of the medial slices alias into the contralateral breast. See FIG. 7A showing an image with aliasing of signal from the contralateral breast into the FOV. This may obscure enhancing lesions or nodes if not corrected using SENSE. The SENSE corrected image and the aliased image component are shown in FIGS. 7B and 7C.

Seventy-three (73) breast abnormalities were found in 45 of the 54 women included in the study. Cases that were described as having multiple foci or multiple masses without giving a specific count were considered as one abnormality for this study. Seven cases (13%) were categorized as being highly suspicious for cancer, sixteen cases (29%) as suspicious, seven cases (13%) as likely benign, but recommended for short-term follow-up, 15 cases (28%) as definitely benign, and 9 cases (17%) were normal.

These findings included lesions that were found in the primary and the contralateral breasts combined. Considering separately, in the cases with contralateral findings, an abnormality was detected in eleven cases (20%). Within these cases, two were diagnosed as suspicious, three cases as likely benign with recommended follow-up, and six cases were diagnosed as benign. Therefore, 11% of 45 cases with a finding in the primary breast had an additional finding in the contralateral breast that was recommended for biopsy or follow-up examination.

FIG. 8 shows a post-contrast phase of a case with an enhancing lesion that was shown to be malignant upon biopsy. FIG. 8A shows a post-contrast breast image with a malignant lesion. A parametric fit was performed on each pixel within a ROI encompassing the lesion, after which the morphological image was analyzed using a color overlay of the $P_1$ parameter in a pixel-by-pixel, 5-parameter fit. Although color cannot be displayed herein, red was used to indicate a high probability of cancer, green a high probability of being benign, and blue for an indeterminate classification (see FIG. 8B; and Dougherty et al., "High Frame-Rate Simultaneous Bilateral DCE-MR Breast Imaging," *Magn. Reson. Med.*, 57:220-225 (2007)), incorporated herein by reference). This analysis was based on earlier results with this kinetic model (Moate et al., supra, 2004). A ROI was taken from the most-enhancing location and is shown with the fitted curve in FIG. 8C. The high temporal resolution allows for a more accurate fit of the data, particularly during the portion of the curve with a high enhancement rate.

Accordingly, as shown, using the methods of the present invention, the visualization of breast lesions was excellent and the high frame-rate allowed more accurate characterization of the contrast kinetics. All exams were deemed diagnostic and exam quality was judged to be similar or higher than that of clinically routine bilateral breast MR imaging techniques. The shorter scan time for the bilateral exam helped to reduce patient motion and thus preserved image quality. The number of detected abnormalities and the classification of those finding were consistent with that seen in the clinical patient population. Abnormalities that required biopsy or follow-up were found in 11% of the women studied, which is consistent with that found by Lee et al., (*Radiology* 226(3): 773-778 (2003)) in a previous study and supports the value of performing bilateral imaging.

Example 2

In light of the foregoing findings that rapid radial dynamic contrast enhanced (DCE) MR breast imaging provides high spatial resolution for architectural assessment, as well as high temporal resolution for better characterization of the kinetic response, lesion characterization was correlated with histopathologic findings to determine the diagnostic performance. The kinetic assessment of breast tumors using the signal enhancement ratio (SER) (Li et al., *Magn. Reson. Med*, 58:572-581 (2007)) has been shown to be a predictor of malignant disease, while being independent of the T1 relaxation time and image intensity scaling. Accordingly, in the present example, DCE-MR images of the breasts were acquired using an undersampled radial trajectory and the kinetic response was assessed using SER.

Methods: One hundred twenty six (126) subjects with palpable or mammographically-visible suspicious findings were recruited and granted IRB approval. From this number, 94 had subsequent pathologic correlation. Images were acquired using 1.5 T MR scanners. The initial 59 cases were acquired using a General Electric Signa and the remaining used a Siemens Sonata scanner. Additionally, the first 103 cases were performed unilaterally while the remaining cases were simultaneous bilateral exams. Subjects were placed in the prone position, with the breasts gently compressed within a dedicated breast coil. The contrast-enhanced images were acquired using a fast 3D spoiled gradient-recalled back-projection sequence using 512 data samples/projection with 48 projections, and 32 phase encoding steps in the slice direction (TR/TE, 10/4; flip angle=20°; ±74 kHz sampling bandwidth). Images were acquired using 24 cm FOV and ~3 mm thick slices. The fat signal was suppressed using a spectral inversion pulse played-out twice per slice group. A high-resolution baseline volume was acquired followed by dynamic imaging started simultaneously with the intravenous injection of 0.1-mmol/kg gadopentetate dimeglumine (Magnevist, Berlex Laboratories, Wayne, N.J.). Contrast was administered over a 10-second interval and followed by a saline flush. Data were acquired over the following 6-minute period with ~15 second temporal resolution.

The images were independently read by two different radiologists (Reader 1 and Reader 2), each experienced in MR breast imaging, and the read images were blinded as to the biopsy results. Each reader placed an region of interest (ROI) on the most enhancing region of the lesion. From the time resolved ROIs, the signal intensity data were obtained and fit to a five parameter modification of a logistic equation of (Moate et al., *Magn Reson Imaging* 22:467-473 (2004)):

$$SI(t) = \frac{P_2 + (P_5 \cdot t)}{\{1 + \exp(-P_4 \cdot (t - P_3))\}} + P_1 \qquad \text{Equation 5}$$

In this heuristic model, $P_1$ is the baseline signal, $P_2$ is related to the magnitude of the peak signal, $P_3$ is the time of the maximum rate of increase of signal, $P_4$ is the maximum rate of signal enhancement and $P_5$ is the terminal slope of the signal enhancement curve. Lesions were considered to be enhancing if their peak intensity increased from baseline by >50%. From the fitted curve, three points were selected: $S_0$ was a baseline, pre-contrast intensity, $S_1$ was the intensity at 60 seconds post-contrast, and $S_2$ was the intensity at 350 seconds. SER was calculated by: $SER=(S_1-S_0)/(S_2-S_0)$. FIG. 10A shows a representative post-contrast breast image with a malignant lesion image and FIG. 10B shows the time signal intensity with the fitted curve on the same plot, wherein contrast injection was initiated after the 8th time point. The curve fit takes advantage of the high temporal resolution and allows for a SER that is less sensitive to signal fluctuations.

Results: Each reader identified 64 enhancing lesions from which time signal intensity plots were measured and fitted. SER was calculated for each case and a ratio 0.8 was chosen as the cutoff between benign (<0.8) and malignant (≧0.8) lesions (FIG. 2). The diagnostic performance for Reader 1 was: Sensitivity=90%, Specificity=97%, PPV=96%, NPV=92%, and the diagnostic accuracy was 94%. For Reader 2, diagnostic performance was: Sensitivity=93%, Specificity=92%, PPV=90%, NPV=94% and the diagnostic accuracy was 92%. There was 1 false positive and three false negatives for this reader. As result, the assessment of breast lesions using the rapid acquisition and model fit in combination with the signal enhancement ratio (SER) provides a more accurate and powerful predictor of benign or malignant disease than has been previously possible with SER alone when the model was not fit.

Since the bilateral breast application of the methods of the present invention is an extension of single slab applications, in alternative embodiments of the invention, the methods also have effectively been applied to imaging lesions of the head/neck, the liver, and for cardiac perfusion imaging. In the alternative, additional uses are found in other simultaneously-imaged paired specimens, e.g., carotid arteries, shoulders, hips, temporo-mandibular joints, separate specimens or multiple samples of any clinical type.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

We claim:

1. A bilateral projection reconstruction method for simultaneous, three dimensional, dynamic contrast-enhanced MR imaging of both breasts of an individual, the method simultaneously in both breasts of the individual comprising the steps of:
   introducing one or more contrast agents into the individual prior to acquiring MR data;
   applying MR spectroscopic settings to tune magnetic field uniformity;
   selectively inverting magnetization from adipose tissue;
   controlling simultaneously exciting magnetization from identified volumes of both breasts using double-side band modulation of an RF slab excitation pulse;
   acquiring high resolution MR data by interleaved radial acquisition for discontinuous volumes of both breasts using multi-coil arrays for signal separation, while under-sampling a number of slice phase encoding steps by a factor of 2;
   reconstructing in-plane encoded image signals from both breast volumes using dynamic k-space weighted image contrast (KWIC) temporal filtering;
   removing signal aliasing from one imaged breast volume to the other using SENSE processing in the slice direction to provide and display three dimensional morphologic images of both breast volumes;
   modeling contrast kinetics using a heuristic model; and
   displaying parameters from the heuristic model as color overlays on the displayed morphologic images.

2. The method of claim 1, wherein the one or more contrast agents comprises paramagnetic metal ions selected from the group consisting of manganese, gadolinium and iron.

3. The method of claim 2, wherein the one or more contrast agents comprises gadolinium.

4. The method of claim 1, wherein the contrast agent is introduced into the individual in an amount sufficient to demonstrate contrast kinetics.

5. The method of claim 4, further comprising archiving the displayed image.

6. The method of claim 5, further comprising transferring the archived image to a tangible storage medium selected from the group consisting of: paper, film, magnetic disk, optical disk, magnetic tape, and non-volatile integrated circuit memory.

7. The method of claim 1, wherein the individual is asymptomatic or symptomatic or at risk for breast cancer, and the images are provided to a radiologist for diagnosing the presence of breast cancer or determining the progress of the disease when the images are compared with earlier images from the individual.

8. The method of claim 1 for signal enhanced, high temporal resolution, the method further comprising the steps of:
   curve fitting the undersampled, acquired MR signal data to a multi-parameter logistic equation; in combination with
   applying a signal enhancement ratio (SER) independent of T1 relaxation time and image intensity scaling.

9. A, bilateral projection reconstruction method for simultaneous, three dimensional, dynamic contrast-enhanced MR imaging of paired bilateral sample volumes in an individual, the method simultaneously in both bilateral volumes comprising the steps of:
   introducing one or more contrast agents into the individual prior to acquiring MR data;
   applying MR spectroscopic settings to tune magnetic field uniformity;
   selectively inverting magnetization from adipose tissue;
   controlling simultaneously exciting magnetization from the identified bilateral volumes using double-side band modulation of an RF slab excitation pulse;
   acquiring high resolution MR data by interleaved radial acquisition for discontinuous volumes, using multi-coil arrays for signal separation, while under-sampling a number of slice phase encoding steps by a factor of 2;
   reconstructing in-plane encoded image signals from both volumes using dynamic k-space weighted image contrast (KWIC) temporal filtering;
   removing signal aliasing from one imaged volume to the other using SENSE processing in the slice direction to provide and display three dimensional morphologic images of both bilateral volumes;
   modeling contrast kinetics using a heuristic model; and
   displaying parameters from the heuristic model as color overlays on the displayed morphologic images.

10. The method of claim 9 for signal enhanced, high temporal resolution, the method further comprising the steps of:
    curve fitting the undersampled, acquired MR signal data to a multi-parameter logistic equation; in combination with
    applying a signal enhancement ratio (SER) independent of T1 relaxation time and image intensity scaling.

11. A system for, bilateral projection reconstruction of simultaneous, three dimensional, dynamic contrast-enhanced MR imaging for paired bilateral sample volumes in an individual, comprising:
    an MRI device, wherein spectroscopic settings tune magnetic field uniformity and magnetization is selectively inverted;
    a double-side band modulator of an RF slab excitation pulse for simultaneously exciting magnetization from the bilateral volumes;
    multi-coil arrays for signal separation of data by interleaved radial acquisition for discontinuous volumes, while under-sampling a number of slice phase encoding steps by a factor of 2;
    means for dynamic k-space weighted image contrast (KWIC) temporal filtering to reconstruct in-plane encoded image signals from both volumes;
    means for using SENSE processing to remove signal aliasing from one imaged volume to the other in the slice direction to provide and to display three dimensional morphologic images of both bilateral volumes; and
    a heuristic model and means to apply the model to display contrast kinetics of the reconstructed image by displaying parameters from the heuristic model as color overlays on the displayed morphologic images.

12. A method of using the system of claim 11, wherein the method comprises applying the provided means for simultaneous, bilateral projection reconstruction, three dimensional, dynamic contrast-enhanced MR imaging of paired bilateral sample volumes in an individual.

13. The system of claim 11, further comprising a means for transferring the viewed image to an archive processor for receiving and storing an archival dataset for long-term storage.

14. The system of claim 11, further comprising a means for archiving the displayed image in a tangible storage medium, which is selected from the group consisting of: paper, film, magnetic disk, optical disk, magnetic tape, and non-volatile integrated circuit memory.

15. A computer program product stored on a tangible storage medium encoding instructions for processing breast images acquired by the method of claim 1, comprising computer code for receiving and computer code for instantiating a transfer off-line of the signal data from the reconstructed in-plane encoded KWIC processed image signals; for reconstructing the images to fit the heuristic model to analyze the contrast kinetics by parametric mapping and color overlays in the displayed morphologic images.

16. The computer program of claim 15, further comprising encoded instructions for generating a time signal enhancement curve for the region of interest or for generating curve parameters for each pixel within the color overlay.

17. The computer program of claim 16, further comprising encoded instructions for creating an archival dataset of the data generated for the bilateral projection reconstruction images and transferring the dataset to an archival medium.

* * * * *